(12) United States Patent
Huebner et al.

(10) Patent No.: US 7,851,762 B2
(45) Date of Patent: Dec. 14, 2010

(54) OPTICAL ANALYSIS DEVICE

(75) Inventors: Joerg Huebner, Dortmund (DE);
Rainer Krage, Herdecke (DE)

(73) Assignee: GfG Gesellschaft fuer Geraetebau mbH, Dortmund (DE)

( * ) Notice: Subject to any disclaimer, the term of this patent is extended or adjusted under 35 U.S.C. 154(b) by 121 days.

(21) Appl. No.: 12/370,861

(22) Filed: Feb. 13, 2009

(65) Prior Publication Data
US 2009/0236524 A1    Sep. 24, 2009

(30) Foreign Application Priority Data
Feb. 14, 2008    (DE) .................. 10 2008 009 100

(51) Int. Cl.
*G01N 21/61* (2006.01)

(52) U.S. Cl. ..................................... 250/343

(58) Field of Classification Search .............. 250/353, 250/343; 356/188, 51, 189, 205, 246
See application file for complete search history.

(56) References Cited

U.S. PATENT DOCUMENTS

| | | | |
|---|---|---|---|
| 3,861,809 A * | 1/1975 | Hall, Jr. .................. | 356/418 |
| 5,923,035 A * | 7/1999 | Winkler et al. ............ | 250/338.5 |
| 6,194,735 B1 * | 2/2001 | Martin ...................... | 250/573 |
| 2003/0106993 A1 * | 6/2003 | Chen et al. ................ | 250/269.1 |
| 2007/0007449 A1 | 1/2007 | Hubner et al. | |
| 2007/0181812 A1 * | 8/2007 | Straub et al. ................ | 250/343 |

FOREIGN PATENT DOCUMENTS

DE        196 04 167 A1    8/1997

OTHER PUBLICATIONS

Zhang et al., "A novel CO2 gas anlayzer based on IR absorption," 2004, Optics and Lasers in Engineering, vol. 42, pp. 219-231.*

* cited by examiner

*Primary Examiner*—David P Porta
*Assistant Examiner*—Kiho Kim
(74) *Attorney, Agent, or Firm*—Roberts Mlotkowski Safran & Cole, P.C.; David S. Safran

(57) ABSTRACT

An optical analysis device that operates according to the principle of radiation absorption, has a housing (2) with at least one radiation-permeable housing element (3), at least one radiation source (4) having a reflector (5) associated with it, at least a first detector (6) and a second detector (7) as well as an external reflector (8) located outside the housing (2), wherein an absorption space is formed by the external reflector (8) and the radiation-permeable housing element (3), and a measuring beam (10) emitted by the radiation source (4) and the reflector (5) returns to the housing (2) again after being reflected by the external reflector (8), and wherein the external reflector (8) has at least one recess (12) that does not reflect the measuring beam and behind which a third detector is arranged for receiving the measuring beam.

16 Claims, 3 Drawing Sheets

OPTICAL ANALYSIS DEVICE

BACKGROUND OF THE INVENTION

1. Field of Invention

The invention relates to an optical analysis device according to the principle of radiation absorption with a housing having at least one radiation-permeable housing element, with at least one radiation source and a reflector assigned to it, with at least a first detector and a second detector and with an external reflector located outside of the housing. An absorption space is formed by the external reflector and the radiation-permeable housing element, wherein a measuring beam emitted by the first radiation source and the first reflector re-enters the housing after reflection on the external reflector.

2. Description of Related Art

Optical analysis devices of the type under consideration exploit the effect of radiation absorption by matter, which is penetrated by electromagnetic radiation. The electromagnetic radiation is generally broadband and covers at least the frequency range in which the substance to be detected acts to absorb radiation. Each substance to be detected shows a characteristic absorption spectrum. The emitted electromagnetic radiation, after passing through the absorption space in which the substance to be detected is located, is relatively strongly attenuated in certain, generally narrowband absorption regions relative to the radiated power of adjacent frequency ranges. While the substances present can be identified via recording of an absorption spectrum, it is also possible to draw conclusions about certain concentrations of the substance via the intensity of the relative attenuation in the absorption range.

Analysis devices of the type under consideration here are used especially for measuring toxic and explosive gases. Here, absorption in the infrared wavelength range characteristic for many gases is used. This absorption of gases and vapors is very specific to a material with respect to its spectral dispersion as well as the degree of absorption. For this reason, the gas-specific absorption is used for identification and determining concentration. Non-dispersive infrared (NDIR) analysis is used here and does not involve spectral decomposition of the emitted electromagnetic radiation. Instead, selective detectors are used which are sensitive only in a limited radiation range, specifically in the range in which the substance to be detected absorbs radiation. Here, optical filters having narrowband transmittance are used to select the radiation of an initially broadband light source, so that they correspond to the absorption of the gas to be measured. The intensity of the infrared radiation is then detected with pyroelectric detectors or thermopiles and analyzed by subsequent electronics, usually a microcontroller.

It can be easily imagined that, when using only one detector, almost no conclusions can be drawn about the actual concentration of the substance which is to be detected, if it is possible for attenuation of the measuring means to be caused in some other way, for example, by the presence of interfering gases and other contaminants in the absorption space. To the same degree, for example, aging-induced intensity attenuation of the radiation source also cannot be detected with only one detector. To compensate for these effects, use of at least two detectors is therefore known in the prior art, of which one detector is sensitive in the absorption range of the substance to be detected and the other detector is sensitive in the frequency range in which absorption by other substances is not possible (reference detector and measuring detector). Certain effects, which adulterate the measurement, can be compensated for by the signal obtained from the measuring detector being referenced to the signal obtained from the reference detector.

Such dual-wavelength systems are used industrially for the protection of people and facilities from toxic and/or explosive gases and vapors. They are often integrated into portable devices, so that it comprises a small and energy-saving system. Just as often, there is a need to be able to simultaneously measure multiple optical detectable gas components with one single device. This exists, for example, in monitoring the danger of explosion from hydrocarbons and the simultaneous measuring of toxic carbon dioxide.

It is known in the prior art to use two independent apparatus in one device. German Patent Application DE 196 04 167 A1 proposes such a sensor device for detecting gas concentrations, which has multiple selective radiation detectors that are arranged annularly at different distances around a broadband radiation source. The arrangement is relatively space consuming and expensive due to the annular arrangement of the detectors having more or less each straight-line, unfolded radiation paths. Only a small dihedral angle section of the radiation source reaches the detectors. This makes high-energy radiators necessary to obtain a good signal to noise ratio.

A construction with two detectors and radiation paths of differing lengths is also proposed according to KR 000190693063 BA. In this arrangement, too, only a small portion of the radiation reaches the detectors, so that the result is a high consumption of energy.

Moreover, there is a problem in that only weakly absorbing components require a longer absorption path compared to strongly absorbing components in order to maintain an identically strong signal at the same material concentration. Depending on the measuring components and the concentration range to be detected, an ideal combination of measuring wavelength range and absorption path always results.

SUMMARY OF THE INVENTION

The present invention is applied to the situation in which different components with different absorption characteristics are to be detected. In particular, an external reflector has at least one recess that does not reflect the measuring beam, and in addition to the usual two detectors, at least a third detector is arranged therein or spatially behind the external reflector. Thus, it is possible to detect different components with differing absorption paths with an optimum utilization of the radiation intensity. Thus, a multi-purpose device is created that can be adapted to different measuring tasks. A portion of the—advantageously collimated—radiation reaches at least a third detector via at least one recess in the external reflector. The remaining radiation is reflected on a curved mirror and passes through the absorption space a second time in order to reach at least a first and second detector. Here, the radiation intensity is measured by the individual detectors in different wavelength ranges. For this purpose, interference filters having band-pass characteristics are arranged in front of the detectors. At least one band-pass area of an interference filter is chosen as a reference channel so that no spectral selective absorption in this range occurs by the medium to be detected or other components containing the measuring medium.

However, at least one further band-pass area lies in the spectral absorption range of a material to be detected as measuring channel. The measured value, which represents a quantity for the concentration of the material to be measured, is preferably produced by formation of quotients from the signal portions of the detectors.

By arranging multiple detectors on both ends of the absorption space, the third or further detector is to be applied for strongly absorbing materials, while the second detector is optimally provided for weaker absorbing materials, since the measuring beam has to pass through the absorption space a second time after reaching the external reflector before it reaches the second detector. The latter is also valid for the first detector (reference detector).

As an alternative, the third detector can be applied for detection in a high concentration range, where the second detector is applied for detection in a low concentration range of the same material. Likewise, instead of the second, third and a further detector a double-detector can be used.

Optionally, a reference channel through a first detector can be used at both detector positions. If the danger of inhomogeneous contamination is low, just one reference channel suffices.

Advantageously, the radiation from the radiation source is collimated by means of its assigned reflector. Here, the reflector assigned to the radiation source is formed as a mirror so that the radiation is directed to the external reflector and the third detector. This can be achieved, for example, by a parabolic mirror surface, or also by a symmetric concave mirror, in particular, a concentrating reflector or curved mirror.

In the external reflector, the mirror surface is formed so that an as large as possible portion of the impacted radiation is directed to the first and second detector. In a simple design, this can be a spherical mirror, in particular, a globe mirror for illuminating a symmetrical detector. The mirrors can be optimized so that both the beams that are only reflected from the external reflector as well as those from the reflector assigned to the radiation source and reflected from the external reflector illuminate the detectors well.

An elliptic beam profile can be generated by an astigmatic curve in order to, e.g., illuminate two neighboring detectors. Here, the detectors are located, for example, in front of the primary line formation of the singly reflected beams and behind the primary line formation of the multiply reflected beams.

In order to better utilize the radiation from the radiation source, the inner walls of the absorption space can be additionally mirrored and formed so that an as large as possible portion of the radiation reaches the third detector with little reflection. Here, for example, a part of the mirrored wall is also elliptically formed, wherein the focal points of the ellipsoid and the third detector are located so that an as large as possible dihedral angle of the radiation arrives at the third detector after just one reflection from the radiation source.

For use in an area with the danger of explosion, the analysis device can be formed in different ignition protection forms. That way, the radiation source can, for example, be attached to the absorption space with a sapphire disc in a pressure-resistant manner in terms of explosion protection standards. Likewise, it is possible to use the radiation source in an increased safety standard. In particular, a use of the radiation source can occur under increased safety "e" according to IEC 60079-7. In particular, miniaturized signal lamps can be applied as an infrared radiation source, these are classified as miscellaneous electric equipment and have to correspond to the relevant building specifications. This way, the radiation source can, for example, be supplied intrinsically safely via mechanically unstressed, soldered connecting wires by a circuit board. The intrinsically safe supply voltage is limited here so that the maximum obtainable surface temperature of the glass bulb remains below the admissible values in order to avoid igniting explosive gases.

In particular, the radiation source is arranged in a metal housing, in particular, one made of stainless steel with a feed-through casting and a form-fit sapphire disc that, even in an impact test with, for example, 4 Joules of impact energy, there is no damage to the glass bulb. Here, the glass bulb is mounted so that a clearance of at least approximately 1 mm is maintained. Thereby, the radiation source is affixed in the housing with an elastic, impact absorbing material, e.g., silicone glue, so that the glass body does not come into immediate contact with the surrounding casting.

The remaining construction of the device can be designed so that lowest possible diffusion times for the material exchange can be obtained. In particular, the absorption space can be protected against contamination using a membrane permeable to gas. As an alternative, the analysis device can be protected against explosion; for example, the absorption space can be protected by a flame trap, e.g., sintered metal, a corresponding housing and a casting. The constructive requirements for explosion protection "d" are stated in IEC 60079-1. It is also possible to combine two independent types of ignition protection redundantly to increase the security and to make execution possible in ex-zone 0.

For example, pyroelectric or thermophile detectors can be used as detectors. In order to minimize interference in the signals, it is advantageous to deal with signal amplification as near as possible to the detectors. The sensor elements can be characterized in regard to signal characteristic, as well as pressure and temperature dependence, the relevant information can be saved in one of the electronic storages assigned to each detector. Here, each detector can be produced in a preferred form with the respective electronics, which include both signal preparation as well as signal processing and additional sensor elements for temperature, moisture and pressure.

The invention is described in detail using the drawing as an example.

DETAILED DESCRIPTION OF THE INVENTION

Figure 1:
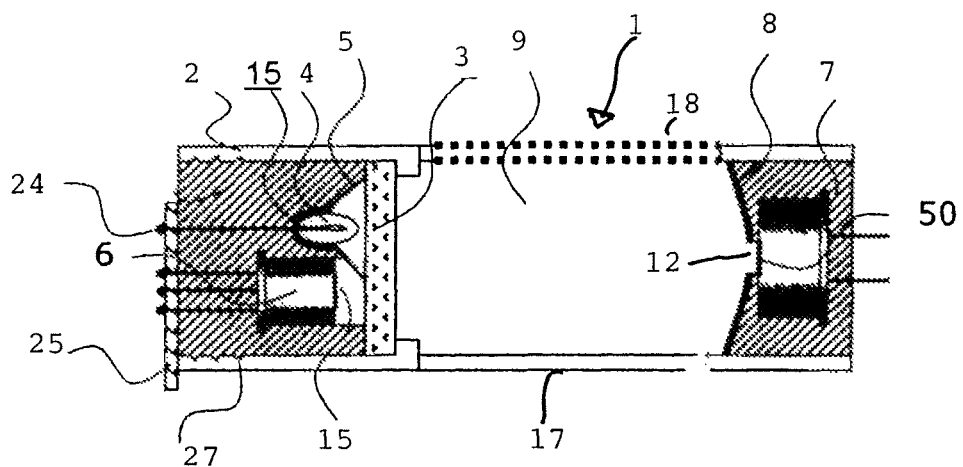
FIG. 1 is a cross-sectional view of an optical analysis device according to the invention.

An optical analysis device 1 operating according to the principle of radiation absorption has a housing 2 with at least one radiation-permeable housing element 3 as well as a radiation source 4 and a reflector 5 assigned to it as well as at least one first detector 6 and a second detector 7 and an external reflector 8 located outside the housing 2. An absorption space 9 is bounded by the radiation-permeable housing element 3 and the external reflector 8 as well as side walls 17, 18.

Figure 5:
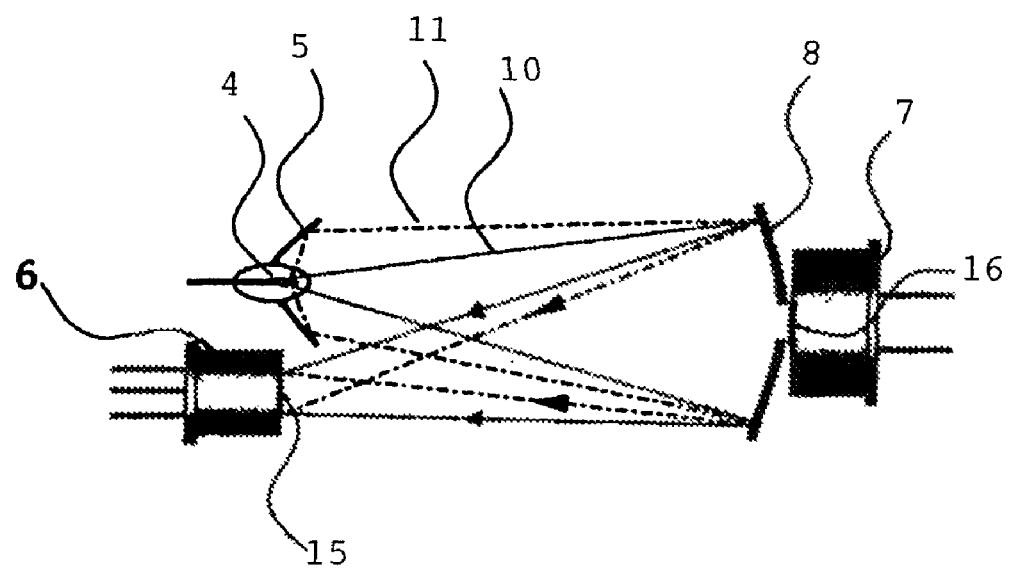
FIG. 5 is a schematic depiction of the beam path from the radiation source via the external reflector to the second detector.

A measuring beam emitted from the radiation source 4 and is reflected back into the housing 2 after reflection by the external reflector 8, as is indicated FIG. 5 by the reference number 11, while a measuring beam 10 coming from the radiation source 4 is not reflected by the associated reflector 5, but is only reflected by the external reflector 8 (path shown by broken lines in FIG. 5). The external reflector 8 has at least one non-reflecting recess 12 according to the invention. A third detector 13 is arranged behind the reflector 8. This third detector 13 is equipped with an interference filter 14, while the first detector 6 and the second detector 7 are also equipped with interference filters 15, 16. Here, the band-pass area of the interference filter 15 is placed before the first detector 6 so that no spectral-selective absorption occurs in this area by means of a medium to be detected or other components contained in the measuring medium. On the other hand, the band-pass areas of the interference filter 16 are formed before the second detector 7 and the interference filter 14, 14' before the third and, where applicable, fourth detector 13, 13' as a measuring channel in the spectral absorption range of a material to be detected.

The measured value from the signal portions of the detectors 6, 7 and 13 and, where applicable, 14 are preferably formed by formation of quotients, which represents a value for the concentration of the material to be examined.

By placing the detectors 7, 13 at both ends of the absorption space 9, the third detector 13 can be applied best for strongly absorbing materials, while the second detector 7 is optimum for weakly absorbing material. As an alternative, the third detector 13 can also be used for detection in higher concentration ranges, whereas the second detector 7 can be used for detection in lower concentration ranges of the same material. Optionally, a reference channel can be used at both detector positions, i.e., within, or respectively, behind the external reflector 8, or just a first detector 6 as a reference channel for detection and compensation of effects, in particular, with inhomogeneous contamination of low danger.

The reflector 5 assigned to the radiation source 4 is formed so that the radiation of the radiation source 4 is directed to the external reflector 8 and the third detector 13. This can be achieved, for example, using a parabolic mirror surface. The mirror surface of the external reflector 8 is formed so that an as large as possible portion of the impacting radiation is directed to the second detector 7. In a simple design, this can be a spherical mirror for illuminating a circularly symmetrical detector.

The mirrors 5, 8 can be further optimized to the effect that both the beams 11 reflected only by the external reflector 8 as well as the beams 10 (shown with dots) reflected from the reflector 5 assigned to the radiation source 4 and the external reflector 8 illuminate the first and second detectors 6 and 7 well, as is shown in FIG. 5.

Figure 2:
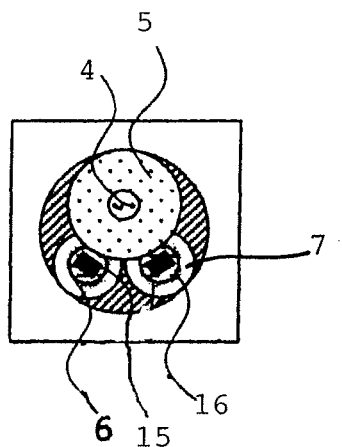
FIG. 2 is a top view of the radiation source, the reflector assigned thereto and the first and second detector.
Figure 3:
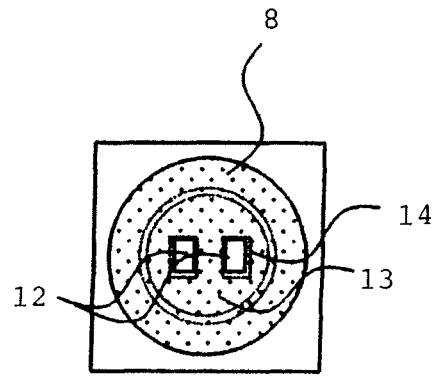
FIG. 3 is a top view of the external reflector with recesses for a third double detector, FIG. 4 a top view of the external reflector with recesses for a third and fourth detector.
Figure 4:
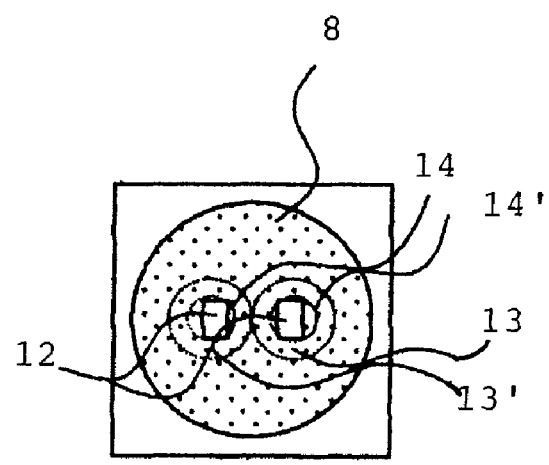
Figure 6:
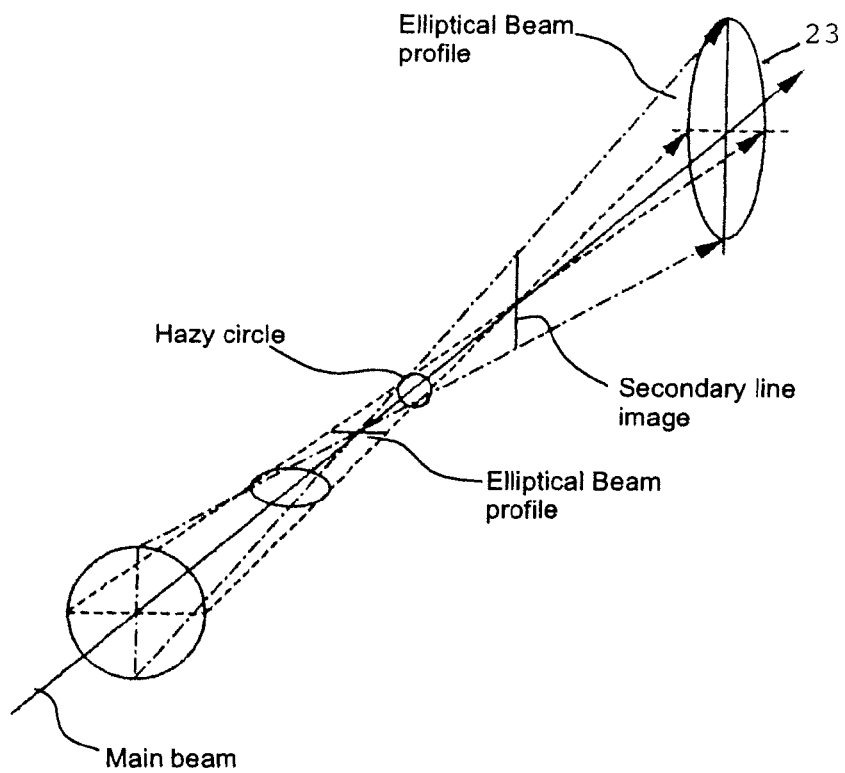
FIG. 6 is a schematic diagram of the beam path using an astigmatically curved, external reflector.

An elliptical beam profile can be achieved using an astigmatic curve in order to, for example, illuminate the two neighboring detectors 6, 7, as is shown in FIG. 2. The detectors 6, 7 are located, there, for example, before the primary line formation of the singly reflected beams 10 and behind the primary line formation of the multiply reflected beams 11, as is shown in FIG. 6.

Figure 7:
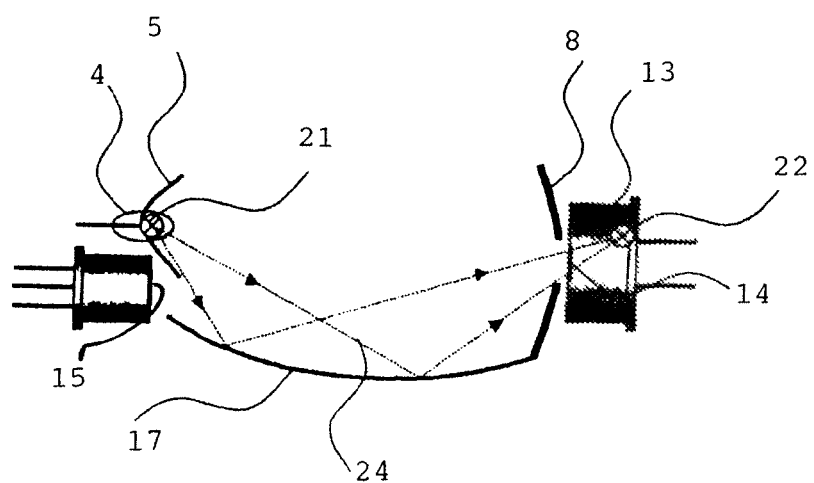
FIG. 7 is a schematic depiction of the beam path using a parabolically formed reflector assigned to the radiation source.

In order to optimally use the radiation source 4, the internal walls 17, 18 of the absorption space 9 are additional mirrored and formed so that an as large as possible portion of the radiation reaches the third detector element 13 with little reflection. Here, a part of the mirrored wall 17, 18 is, for example, elliptically formed as is shown in FIG. 7. In this case, the focus points 21, 22 of the ellipsoid 23 are located in the area of the radiation source 4 and the third detector 13 so that a large as possible dihedral angle of the beams 24 reach the third detector 13 from the radiation source 4 after just one reflection on the mirrored side walls 17, 18, as is shown in FIG. 7.

The radiation-permeable housing element 3 can, for example, be formed as a sapphire disc in order to make the radiation source 4 pressure resistant in terms of explosion protection standards. The radiation source 4 can also occur under increased safety. Here, the radiation source 4 is intrinsically safely supplied via mechanically unstressed, soldered connecting wires 24 by a circuit board 25. The intrinsically safe supply voltage is limited so that the maximum attainable surface temperature of the glass bulb of the radiation source is kept below the admissible value for avoiding the ignition of an explosive gas. The radiation source 4 is situated in a metal housing 2, which e.g., can be made of stainless steel, and has a feed-through casting and a radiation-permeable housing element 3 formed as a form-fit sapphire disc 27. A distance of at least approximately 1 mm is kept between the glass bulb of the radiation source 4 and the sapphire disc 3 so that when testing impact with 4 Joules of impact energy is applied, there is no damage to the glass bulb. The radiation source 4 is affixed in the housing with elastic, impact energy absorbing material, for example, a silicone glue 26 so that there is no immediate contact with the surrounding casting.

The absorption space 9, itself, can be protected against contamination using a membrane 20 that is permeable to gases. In addition, the analysis device 1 is designed so that lowest possible diffusion times for the material exchange in the absorption space 9 can be achieved.

Of course, the invention is not limited to the shown embodiments. Further embodiments are possible without abandoning the fundamental idea.

What is claimed is:

1. A radiation absorption optical analysis device, comprising:
   a housing with at least one radiation-permeable housing element,
   at least one radiation source,
   a reflector associated with the at least one radiation source,
   at least one first detector,
   a second detector, and
   an external reflector located outside the housing,
   wherein an absorption space is formed between the external reflector and the at least one radiation-permeable housing element,
   wherein the radiation source and the reflector are positioned relative to the external reflector so that a measuring beam emitted by the radiation source will be reflected back to the housing after being reflected by the external reflector,
   wherein the external reflector has at least one recess through which a measuring beam can pass, and
   wherein a third detector is arranged behind the recess for receiving the measuring beam.

2. Optical analysis device according to claim 1, wherein the associated with the radiation is adapted to collimate radiation from the radiation source.

3. Optical analysis device according to claim 1, wherein interference filters having band-pass characteristics are arranged in front of the detectors.

4. Optical analysis device according to claim 1, wherein at least one band-pass area of an interference filter is provided as a reference channel for preventing spectral-selective absorption by means a medium to be detected or components contained therein.

5. Optical analysis device according to claim 1, wherein at least one band-pass area of an interference filter in the spectral absorption range of a material to be detected is provided as a measuring channel.

6. Optical analysis device according to claim 1, wherein the reflector associated with the radiation source is a symmetrical concave mirror.

7. Optical analysis device according to claim 1, wherein the reflector associated with the radiation source is a concentrating reflector or curved mirror.

8. Optical analysis device according to claim 1, wherein the at least one first detector and the second detector are arranged within the housing directly adjacent to the radiation source, and wherein the external reflector adapted to reflect a focused measuring beam reflected that will miss the reflector associated with the radiation source so as to directly reach the first and second detectors.

9. Optical analysis device according to claim 1, wherein the external reflector is a spherical mirror.

10. Optical analysis device according to claim 1, wherein the reflector associated with the radiation source is a parabolic mirror.

11. Optical analysis device according to claim 1, wherein the external reflector is adapted to return an elliptically formed measuring beam to the first and second detectors.

12. Optical analysis device according to claim 1, wherein inner walls of the absorption space are mirrored and formed so that an as large as possible portion of the radiation from the radiation source will reach the third detector with little reflection.

13. Optical analysis device according to claim 12, wherein at least a part on the inner walls are elliptically shaped.

14. Optical analysis device according to claim 1, wherein the radiation source is arranged in the housing in a pressure resistant manner.

15. Optical analysis device according to claim 1, wherein a sapphire disc is arranged in front of the radiation source facing into the absorption space.

16. Optical analysis device according to claim 1, wherein the radiation source is an infrared radiation source comprised of miniaturized signal lamps.

* * * * *